US008048914B2

(12) United States Patent  
An et al.

(10) Patent No.: US 8,048,914 B2
(45) Date of Patent: Nov. 1, 2011

(54) **METHODS FOR ISOLATION OF TRIPTOLIDE COMPOUNDS FROM *TRIPTERYGIUM WILFORDII***

(75) Inventors: Jinhua An, Palo Alto, CA (US); Rensheng Xu, Los Altos, CA (US); John H. Musser, San Carlos, CA (US)

(73) Assignee: Pharmagenesis, Inc., Redwood City, CA (US)

( * ) Notice: Subject to any disclaimer, the term of this patent is extended or adjusted under 35 U.S.C. 154(b) by 1117 days.

(21) Appl. No.: 10/588,883

(22) PCT Filed: Feb. 7, 2005

(86) PCT No.: PCT/US2005/003888
§ 371 (c)(1),
(2), (4) Date: May 8, 2007

(87) PCT Pub. No.: WO2005/077008
PCT Pub. Date: Aug. 25, 2005

(65) Prior Publication Data
US 2007/0282114 A1    Dec. 6, 2007

Related U.S. Application Data

(60) Provisional application No. 60/543,236, filed on Feb. 9, 2004.

(51) Int. Cl.
*A61K 31/34* (2006.01)
(52) U.S. Cl. ...................................... 514/468
(58) Field of Classification Search .................. 514/468
See application file for complete search history.

(56) References Cited

U.S. PATENT DOCUMENTS

| | | | |
|---|---|---|---|
| 4,005,108 A | 1/1977 | Kupchan et al. |
| 5,192,817 A | 3/1993 | Takaishi et al. |
| 5,294,443 A | 3/1994 | Lipsky et al. |
| 5,430,054 A | 7/1995 | Qian et al. |
| 5,468,772 A | 11/1995 | Xu et al. |
| 5,580,562 A | 12/1996 | Lipsky et al. |
| 5,648,376 A | 7/1997 | Strobel et al. |
| 5,663,335 A | 9/1997 | Qi et al. |
| 5,759,550 A | 6/1998 | Wiedmann et al. |
| 5,843,452 A | 12/1998 | Wiedmann et al. |
| 5,919,816 A | 7/1999 | Hausheer et al. |
| 5,962,516 A | 10/1999 | Qi et al. |
| 5,972,998 A | 10/1999 | Jung et al. |
| 6,004,999 A | 12/1999 | Jung et al. |
| 6,011,042 A | 1/2000 | Greenwald et al. |
| 6,103,875 A | 8/2000 | Martinez-Miller et al. |
| 6,150,539 A | 11/2000 | Musser |
| 6,294,546 B1 | 9/2001 | Rosen et al. |
| 6,329,148 B1 | 12/2001 | Rosen et al. |
| 6,458,537 B1 | 10/2002 | Staub et al. |
| 6,537,984 B2 | 3/2003 | Rosen et al. |
| 6,548,537 B1 | 4/2003 | Dai et al. |
| 6,569,893 B2 | 5/2003 | Dai et al. |
| 6,599,499 B1 | 7/2003 | Rosen et al. |
| 6,620,843 B2 | 9/2003 | Fidler et al. |
| 6,777,441 B2 | 8/2004 | Wang et al. |
| 6,943,259 B2 | 9/2005 | Dai et al. |
| 7,019,151 B2 | 3/2006 | Dai et al. |
| 7,098,348 B2 | 8/2006 | Dai et al. |
| 7,417,069 B2 | 8/2008 | Dai et al. |
| 2002/0077350 A1 | 6/2002 | Babish et al. |
| 2002/0099051 A1 | 7/2002 | Fidler et al. |
| 2004/0018260 A1 | 1/2004 | Ren et al. |
| 2004/0152767 A1 | 8/2004 | Dai et al. |
| 2004/0198808 A1 | 10/2004 | Dai et al. |
| 2004/0235943 A1 | 11/2004 | Dai et al. |
| 2005/0288645 A1 | 12/2005 | LaVon |
| 2007/0244080 A1 | 10/2007 | Fidler et al. |
| 2007/0249048 A1 | 10/2007 | Dai et al. |
| 2007/0282114 A1 | 12/2007 | An et al. |
| 2008/0287530 A1 | 11/2008 | Yuan et al. |

FOREIGN PATENT DOCUMENTS

| | | |
|---|---|---|
| CN | 1052859 A | 7/1991 |
| CN | 1317248 A | 10/2001 |
| EP | 0 156 643 B1 | 10/1985 |
| JP | 03 178977 | 8/1991 |
| WO | WO 94/26265 A1 | 11/1994 |
| WO | WO 98/52933 A1 | 11/1998 |
| WO | WO 98/52951 A1 | 11/1998 |
| WO | WO 00/12483 A1 | 3/2000 |
| WO | WO 00/63212 | 10/2000 |
| WO | WO 02/070472 A1 | 9/2002 |
| WO | WO 02/074759 A1 | 9/2002 |
| WO | WO 03/101951 A2 | 12/2003 |
| WO | WO 2005/000291 A1 | 1/2005 |
| WO | WO 2005/020887 A2 | 3/2005 |
| WO | WO 2005/062913 A2 | 7/2005 |

(Continued)

OTHER PUBLICATIONS

M. Beroza Journal of the American Chemical Society 1952, 74, 1585-1588.*
M. Beroza Journal of the American Chemical Society 1953, 75, 44-49.*
R Milanova—Biotransformation of Synthetic Abietane Diterpenes by Filamentous Fungi. Novel Routes to the Familty of Diterpenes Isolated From TW 1995—Dissertation.*
Anderson, Wayne K. et al., "Synthesis, Evaluation of Chemical Reactivity, and Murine Antineoplastic Activity of 2-Hydroxy-5-(3,4-dichlorophenyl)-6,7-bis(hydroxymethyl)-2,3-dihydro-1*H*-pyrrolizine Bis(2-propylcarbamate) and 2-Acyloxy Derivatives as Potential Water-Soluble Prodrugs[1]", *J. Med. Chem.*, 26:1333-1338 (1983).

(Continued)

*Primary Examiner* — Janet Andres
*Assistant Examiner* — John Mabry
(74) *Attorney, Agent, or Firm* — King & Spalding LLP; Susan J. Myers Fitch; Peter J. Dehlinger

(57) ABSTRACT

Methods for extraction, isolation, and purification of therapeutically useful compounds from *Tripterygium wilfordii* are described. Extraction steps employing aqueous base and a hydrocarbon solvent, respectively, are found to increase the efficiency of the process and reduce the amount of material that must be removed by chromatography.

17 Claims, No Drawings

FOREIGN PATENT DOCUMENTS

| | | |
|---|---|---|
| WO | WO 2005/084365 A2 | 9/2005 |
| WO | WO 2006/012204 A2 | 2/2006 |

OTHER PUBLICATIONS

Aumuller, G. et al., "Intermediate filaments in sertoli cells", *Microscopy Research and Technique*, 20:50-72(1992).

Becker, K. et al., "Thioredoxin reductase as a pathophysiological factor and drug target", *Eur. J. Biochem.*, 267(20):6118-6125 (2000).

Berg, D. et al., "14-3-3 Proteins in the nervous system", *Nature Reviews Neuroscience*,. 4:752-62 (2003).

Britton, R. et al., "New okadaic acid analogues from the marine sponge *Merriamum oxeato* and their effect on mitosis", *J. Nat. Prod.*, 66:838-43 (2003).

Chang, W-T. et al., "Triptolide and chemotherapy cooperate in tumor cell apoptosis. A role for the p53 pathway", *The Journal of Biological Chemistry*, 279(3):2221-2227 (2001).

Chen et al., "Mechanisms of tolerance induced by PG490-88 in a bone marrow transplantation model", *Transplantation*, 73(1):115 (2002).

Chen et al., "Prevention of graft-versus-host disease by a novel immunosuppressant, PG490-88, through inhibition of alloreactive T cell expansion", *Transplantation*, 70(10):1442-1447 (2000).

Cheng, X.X. et al., Yao Xue Xue Bao, *ACTA Pharmaceutica Sinica*, 37:339-342 (2002) (English Abstract translation).

Dan et al., "Studies on triepoxide analogs of triptolide", *Tetrahedron Letters*, 38(39):6865-6868 (1997).

De Groot Franciscus M. H. et al., "Synthesis and Biological Evaluation of 2'-Carbamate-Linked and 2'-Carbonate-Linked Prodrugs of Paclitaxel: Selective Activation by the Tumor-Associated Protease Plasmin", *J. Med. Chem.*, 43:3093-3102 (2000).

De Quan Yu et al., "Chemical Transformation of Triptolide", *Chinese Chemical Letters*, 2(12):937-940 (1991).

Dittert, L.W. et al., "Acetaminophen Prodrugs I Synthesis, Physicochemical Properties, and Analgesic Activity", *Journal of Pharmaceutical Sciences*, 57(5):774-780 (1968).

Dittert, L.W. et al., "Acetaminophen Prodrugs II Effect of Structure and Enzyme Source on Enzymatic and Nonenzymatic Hydrolysis of Carbonate Esters", *Journal of Pharmaceutical Sciences*, 57(5):780-783 (1968).

Englebienne et al., *Drug Design Reviews—Online*, "The Place of Biosteric Sila Substitution in Drug Design", 2 pages (2005).

Fidler, J.M. et al., "PG490-88, a derivative of triptolide, causes tumor regression and sensitizes tumors to chemotherapy", *Molecular Cancer Therapeutics*, 2(9):855-62 (2003).

Fidler, J.M. et al., "Immunosuppressive activity of the Chinese medicinal plant *Tripterygium wilfordii*. III. Suppression of graft-versus-host disease in murine allogeneic bone marrow transplantation by the PG27 extract", *Transplantation*, 74(4):445-457 (2002).

Fruman, D.A. et al., "Phosphoinositide Kinases", *Ann. Rev. Biochem.*, 67:481-507 (1998).

Fu et al., "14-3-3 Proteins: Structure, Function, and regulation", *Ann. Rev. Pharmacol. Toxicol.*, 40:617-47 (2000).

Gabbiani, G., "The myofibroblast in wound healing and fibrocontractive diseases", *Journal of Pathology*, 200:500-503 (2003).

Garcia, A. et al., "Serine/threonine protein phosphatases PP1 and PP2A are key players in apoptosis", *Biochimie*, 85:721-726 (2003).

Gilles, C. et al., "Transactivation of vimentin by beta-catenin in human breast cancer cells", *Cancer Research*, 63(10):2658-2664 (2003).

Gleichmann, E. et al., "Graft-versus-host reactions: clues to the etiopathology of a spectrum of immunological diseases", *Immunology Today*, 5(11):324-332 (1984).

Goto, Y. et al., "Augmented cytoplasmic Smad4 induces acceleration of TGF-beta1 signaling in renal tubulointerstitial cells of hereditary nephrotic ICGN mice with chronic renal fibrosis; possible role for myofibroblastic differentiation", *Cell Tissue Res.*, 315:209-221 (2004).

Gross, T.J. and Hunninghake, G.W., "Idiopathic pulmonary fibrosis", *N. Engl. J. Med.*, 345(7):517-525 2001.

Hansen, Kristian T. et al., "Carbamate Ester Prodrus of Dopaminergic Compounds: Synthesis, Stability, and Bioconversion", *Journal of Pharmaceutical Sciences*, 80(8):793-798 (1991).

Hansen, Laila B. et al., "Ketobemidone prodrugs for buccal delivery", *Acta Pharm. Nord.*, 3(2):77-82 (1991).

He, Q. et al., "Neuroprotective eggects of *Tripterygium wilfordii* Hook F Monomer $T_{10}$ on glutamate induced PC12 cell line damage and its mechanism", *Beijing Da Xue Xue Bao, Journal of Peking University (Health Sciences)*, 35(3):252-5 (Jun. 2003) (English Abstract Translation).

Houtman, J.C. et al., "Early phosphorylation kinetics of proteins involved in proximal TCR-mediated signaling pathways", *Journal of Immunology*, 175(4):2449-2458 (2005).

Huang, Tien L. et al., "Hydrolysis of Carbonates, Thiocarbonates, Carbamates, and Carboxylic Esters of $\alpha$-Naphthol, $\beta$-Naphthol, and *p*-Nitrophenol by Human, Rat, and Mouse Liver Carboxylesterases", *Pharmaceutical Research*, 10(5):639-648 (1993).

Jiang, X.-H. et al., "Functional p53 is required for triptolide-induced apoptosis and AP-1 and nuclear factor-kappaB activation in gastric cancer cells",*Oncogene*, 20(55):8009-8018 (2001).

Jerums, G. et al., "Evolving concepts in advanced glycation, diabetic nephropathy, and diabetic vascular disease", *Archives of Biochemistry and Biophysics*, 419(1):55-62 (2003).

Jiarun, Z. et al., "Screening of active anti-inflammatory, immunosuppressive and antifertility components of *Tripterygium wilfordii*", ACTA Academiae Medicinae Sinicae 13(6):391-397 (English Abstract only) (1991).

Jones, S.L. et al. "A role for the actin-bundling protein L-plastin in the regulation of leukocyte integrin function", *Proc. Natl. Acad. Sci. USA*, 95(16):9331-9336 (1998).

Kahns, A. M. et al., "Prodrugs of Peptides. 18. Synthesis and Evaluation of Various Esters of Desmopressin (dDAVP)", *Pharmaceutical Research*, 10(1):68-74 (1993).

Kershenobich, D. et al., "Concise Review: Liver fibrosis and inflammation. A review", *Annals of. Hepatology*, 2(4):159-163 (2003).

Keyser, F. D. et al., "The role of T cells in Rheumatoid Arthritis", *Clinical Rgeumatology*, 14(Suppl 2):5-9 (1995).

Khanna, A.K. and Mehta, M.R., "Targeted in vitro and in vivo gene transfer into T lymphocytes: potential of direct inhibition of alloimmune activation", *BMC Immunology*, 7(26):1-10 (2006).

Korngold, B. and Sprent, J. "Lethal graft-versus-host disease after bone marrow transplantation across minor histocompatibility barriers in mice. Prevention by removing mature T cells from marrow", *J. Exp. Med.*, 148:1687-98 (1978).

Kurz, E.U. et al., "Modulation of human DNA topoisomerase IIalpha function by interaction with 14-3-3epsilon", *The Journal of Biological Chemistry*, 275(18):13948-13954 (2000).

Kutney, J.P. et al., "Studies with plant cell cultures of the Chinese herbal plant, *Tripterygium wilfordii*, Synthesis and biotransformation of diterpene analogues", *Heterocycles*, 44(1):2-11 (1997).

Larribere, L. et al., "PI3K mediates protection against TRAIL-induced apoptosis in primary human melanocytes", *Cell Death and Differentiation*, 11(10):1084-1091 (2004).

Leonard, C.T. et al., "PG490-88, a derivative of triptolide, attenuates obliterative airway disease in a mouse heterotopic tracheal allograft model", *Journal of Heart and Lung Transplantation*, 21(12):1314-1318 (2002).

Leuenroth, S.J. and Crews, C.M., "Studies on calcium dependence reveal multiple modes of action for triptolide", *Chemistry and Biology*, 12(12):1259-1268 (2005).

Li, K.K. and Fidler, J.M., "PG490-88 erxerts 1-16 potent anticancer activity alone and in combination therapy in a nude mouse xenograft model", Proceedings of the American Association for Cancer Research Annual Meeting Mar. 2001, 42:73, Abstract #391 (2001).

Li, F-Q. et al., "Neurotrophic and neuroprotective effects of tripchlorolide, an extract of Chinese herb *Tripterygium wilfordii* Hook F, on dopaminergic neurons", *Experimental Neurology*, 179(1):28-37 (2003).

Li, F-Q. et al., "Triptolide, a Chinese herbal extract, protects dopaminergic neurons from inflammation-mediated damage through inhibition of microglial activation", *Journal of Neuroimmunology*, 148(1-2):24-31 (2004).

Lin, C.S. et al., "Upregulation of L-plastin gene by testosterone in breast and prostate cancer cells: identification of three cooperative androgen receptor-binding sequences", *DNA Cell Biology*, 19(1):1-7 (2000).

List, A.F. et al., "Vascular endothelial growth factor receptor-1 and receptor-2 initiate a phosphatidylinositide 3-kinase-dependent clonogenic response in acute myeloid leukemia cells.", *Experimental Hematology*, 32(6):526-535 (2004).

Lovell, M.A. et al. "Decreased thioredoxin and increased thioredoxin reductase levels in Alzheimer's disease brain", *Free Radical Biology & Medicine*, 28(3):418-27 (2000).

Lundstrom, J. et al., "A Pro to His mutation in active site of thioredoxin increases its disulfide-isomerase activity 10-fold. New refolding systems for reduced or randomly oxidized ribonuclease", *The Journal of Biological Chemistry*, 267(13):9047-9052 (1992).

Lundy, S.K. et al., "Cells of the synovium in rheumatoid arthritis", *Arthritis Research & Therapy*, 9(1):1-11 (2007).

Ma et al., "Isolation of 17-hydroxytriptolide and analogs as drugs", ACTA Pharmaceutica Sinica, 28(2):110-115 (1993). (English Abstract translation).

Mason et al., "Pharmacological therapy fir idiopathic pulmonary fibrosis", *Am. J. Respir. Crit. Care Med.*, 160:1771-1777 (1999).

Masters, S.C. and Fu, H., "14-3-3 Proteins mediate an essential anti-apoptotic signal", *The Journal of Biological Chemistry*, 276(48):45193-45200 (2001).

Matlin, S.A. et al., "Male antifertility compounds from *Tripterygium wilfordi Hook F.*", *Contraception*, 47:387-400 (1993).

Mesa, R.A. et al., "In vitro antiproliferative activity of the farnesyltransferase inhibitor R115777 in hematopoietic progenitors from patients with myelofibrosis with myeloid metaplasia", *Leukemia*, 17(5):849-55 (2003).

Gu, Ming et al., "Effect of Chinese herb *Tripterygium wilfordii* Hook F monomer triptolide on apoptosis of PC12 cells induced by Aβ1-42" *ACTA Physiologica Sinica*, 56(1):73-78 (2004) (English Abstract translation).

Murase, N. et al., "Hamster-to-rat heart and liver xenotransplantation with FK506 plus antiproliferative drugs", *Transplantation*, 55(4):701-708 (1993).

Nassar, M. N. et al., "Effects of Structural Variations on the Rates of Enzymatic and Nonenzymatic Hydrolysis of Carbonate and Carbamate Esters", *Journal of Pharmaceutical Sciences*, 81(3):295-298 (1992).

Ning, L. et al., "Biotransformation of triptolide by *Cunninghamella blakesleana*", *Tetrahedron*, 59(23):4209-4213 (2003).

Ono, K. and Lindsey, E.S., "Improved technique of heart transplantation in rats", *Journal of Thoracic and Cardiovascular Surgery*, 57(2):225-29 (1969).

Ory, S. et al., "Protein phosphatase 2A positively regulates Ras signaling by dephosphorylating KSR1 and Raf-1 on critical 14-3-3 binding sites", *Current Biology*, 13(16):1356-1364 (2003).

Otsuka, M. et al., "Differential expression of the L-plastin gene in human colorectal cancer progression and metastasis", *Biochemical and Biophysical Research Communications*, 289(4):876-881 (2001).

Pei, J-J. et al. "Okadaic-acid-induced inhibition of protein phosphatase 2A produces activation of mitogen-activated protein kinases ERK1/2, MEK1/2, and p70 S6, similar to that in Alzheimer's disease", *American Journal of Pathology*, 163(3):845-858 (2003).

Powis, G. and Montfort, W.R., "Properties and biological activities of thioredoxins", *Ann.Rev. Pharmacol. Toxicol.*, 41:261-295 (2000).

Qiu, D. and Kao, P.N., "Immunosuppressive and anti-inflammatory mechanisms of triptolide, the principal active diterpenoid from the Chinese medicinal herb *Tripterygium wilfordii* Hook. f.", *Drugs R&D*, 4(1):1-18 (2003).

Qiu, D. et al., "Immunosuppressant PG490 (triptolide) inhibits T-cell interleukin-2 expression at the level of purine-box/nuclear factor of activated T-cells and NF-kappaB transcriptional activation", *The Journal of Biological Chemistry*, 274(19):13443-13450 (1999).

Redpath, N. T. et al., "Regulation of translation elongation factor-2 by insulin via a rapamycin-sensitive signalling pathway", *The EMBO Journal*, 15(9):2291-2297 (1996).

Reichert, T.E. et al., "Interleukin-2 expression in human carcinoma cell lines and its role in cell cycle progression", *Oncogene*, 19(4):514-525 (2000).

Sato, S. et al., "Modulation of Akt kinase activity by binding to Hsp90 ", *Proc Natl Acad Sci USA*, 97(20):10832-10837 (2000).

Savolainen, Jouko et al., "Synthesis and in vitro/in vivo evaluation of novel oral N-alkyl- and N,N-dialkyl-carbamate esters of entacapone", *Life Sciences*, 67:205-216 (2000).

Schlesinger, C. et al., "Constrictive (obliterative) bronchiolitis: diagnosis, etiology, and a critical review of the literature", *Annals of Diagnostics Pathology*, 2(5):321-34 (1998).

Schlesinger, C. et al., "Constrictive (obliterative) bronchiolitis ", *Current Opinion in Pulmonary Medicine*, 4:288-293 (1998).

Schwaller, M. et al., "Reduction-reoxidation cycles contribute to catalysis of disulfide isomerization by protein-disulfide isomerase", *The Journal of Biological Chemistry*, 278(9):7154-7159 (2003).

Selman, M. et al., "Idiopathic pulmonary fibrosis: prevailing and evolving hypotheses about its pathogenesis and implications for therapy ",*Ann. Intern. Med.*, 134:136-151 (2001).

Shamon, L.A. et al., "Evaluation of the mutagenic, cytotoxic, and antitumor potential of triptolide, a highly oxygenated diterpene isolated from *Triptetygium wilfordifi*", *Cancer Letters*, 112:113-117 (1997).

Shanmuganathan et al., "Enhanced brain delivery of an anti-HIV nucleoside 2'-F-ara-ddI by xanthine oxidase mediated biotransformation", *J. Med. Chem.*, 37:821-827 (1994).

Shevchenko, A. et al., "Mass spectrometric sequencing of proteins silver-stained polyacrylamide gels", *Anal. Chem.*, 68(5):850-858 (1996).

Shevchenko, A. et al., "Linking genome and proteome by mass spectrometry: large-scale identification of yeast proteins from two dimensional gels", *Proc Natl Acad Sci USA*, 93:14440-14445 (1996).

Show, M. et al., "Reduced intratesticular testosterone concentration alters the polymerization state of the Sertoli cell intermediate filament cytoskeleton by degradation of vimentin", *Endocrinology*, 144(12):5530-6 (2003).

Solit, D. et al., "Hsp90 as a therapeutic target in prostate cancer", *Seminars in Oncology*, 30(5):709-16 (2003).

Sontag et al., "Protein phosphatase 2A is a critical regulator of protein kinase C zeta signaling targeted by SV40 small t to promote cell growth and NF-kappaB activation", *The EMBO Journal*, 16(18):5662-5671 (1997).

Stella, V.J. et al., "Prodrugs, Do they have advantages in Clinical Practice ?", *Drugs*, 29:455-473 (1985).

Tolstonog et al., "Role of the intermediate filament protein vimentin in delaying senescence and in the spontaneous immortalization of mouse embryo fibroblasts", *DNA and Cell Biology*, 20(9):509-29(2001).

Tunek, Anders et al., "Hydrolysis of $^3$H-Bambuterol, A Carbamate Prodrug of Terbutaline, in Blood from Humans and Laboratory Animals In Vitro", *Biochemical Pharmacology*, 37(20):3867-3876 (1988).

Van Tamelen et al., "Biogenetic-type total synthesis of (.+, -31 ) -triptonide and (.+-31 .) -triptolide", STN International Database, CAPLUS database Document No. 96:143107 2 pages (1982).

Vierling et al., "Highly fluorinated amphiphiles as drug and gene carrier and delivery systems", *Journal of Fluorine Chemistry*, 107:337-354 (2001).

Waller, D.G. and George, C.F., "Prodrugs", *Br. J. Clin. Pharmac.*, 28:497-507 (1989).

Wahlgren, C-F. et al, "Itch and inflammation induced by intradermally injected interleukin-2 in atopic dermatitis patients and healthy subjects", *Arch Dermatol Res.*, 287(6):572-580 (1995).

Wang, Z. et al., "Altered distribution of Sertoli cell vimentin and increased apoptosis in cryptorchid rats", *Journal of Pediatric Surgery*, 37(4):648-652 (2002).

Wang, J. et al., "Immunosuppressive activity of the Chinese medicinal plant *Tripterygium wilfordii*. I. Prolongation of rat cardiac and renal allograft survival by the PG27 extract and immunosuppressive synergy in combination therapy with cyclosporine", *Transplantation*, 70(3):447-455 (2000).

Wang, J. and Morris, R.E., "Effect of splenectomy and mono- or combination therapy with rapamycin, the morpholinoethyl ester of mycophenolic acid and deoxyspergualin on cardiac xenograft survival", *Transplantation Proceedings*, 23(1):699-702 (1991).

Wang, X. et al., "Mechanism of triptolide-induced apoptosis: Effect on caspase activation and Bid cleavage and essentiality of the hydroxyl group of triptolide", *J. Mol. Med.*, 84:405-415 (2006).

Weibel, Helle et al., "Macromolecular prodrugs IXX. Kinetics of hydrolysis of benzyl dextran carbonate ester conjugates in aqueous buffer solutions and human plasma", *Acta Pharm. Nord.*, 3(3):159-162 (1991).

Weng, G. et al. "Advances in studies on apoptosis induced by *Tripterygium wilfordii*", *Chinese Traditional and Herbal Drugs*, 33(11):1053-1054 (2002) (No English Abstract Translation).

Whitesell, L. et al., "The stress response: implications for the clinical development of hsp90 inhibitors", *Current Cancer Drug Targets*, 3(5):349-358 (2003).

Yamagishi, S. et al., "Advanced glycation end products inhibit de novo protein synthesis and induce TGF-beta overexpression in proximal tubular cells", *Kidney International*, 63(2):464-473 (2003).

Yamamoto, R. et al., "Pharmaceutical Studies on water-Soluble corticosteroid derivatives I. Stability of Hydrocortisone 21 Hemiesters in Solution", Journal of the Pharmaceutical Society of Japan, 46(8):855-862 (1971).

Yang, S. et al., "Triptolide Induces apoptotic death of T lymphocyte", *Immunopharmacology*, 40:139-149 (1998).

Yang, J. et al., "Disruption of the EF-2 kinase/Hsp90 protein complex: a possible mechanism to inhibit glioblastoma by geldanamycin", *Cancer Research*, 61(10):4010-4016 (2001).

Yang, S. et al., "Triptolide Inhibits the Growth and Metastasis of Solid Tumors", *Molecular Cancer Therapeutics*, 2:65-72 (2003).

Yano, H. et al., "Inhibition of histamine secretion by wortmannin through the blockade of phosphatidylinositol 3-kinase in RBL-2H3 cells", *The Journal of Biological Chemistry*, 268(34):25846-25856 (1993).

Yuan, G-H. et al., "Characterization of cells from pannus-like tissue over articular cartilage of advanced osteoarthritis", *OsteoArthritis and Cartilage*, 12(1):38-45 (2004).

Zheng et al., "Screening of active iantiinflammatory, immunosuppressive and antifertility components of *Tripterygium wilfordii*", Chemiacl Abstracts 117(9): Abstract No. 83085a (1992).

Zhou, H-F. et al., "Triptolide inhibits TNF-alpha, IL-1 beta and NO production in primary microglial cultures", *Neuroreport*, 14(7):1091-5 (2003).

Zhou, Y.X. et al., *Ai Zheng* 21:1108-8 (2002).

Chen, J-Y et al., "Improved Preparation of Triptolide Extract", *Chinese Journal of Pharmaceutcials*, 20(5):195 and 200 (Dec. 31, 1989) (English translation of abstract and concise explanation of relevance from Foreign Office Action).

Textbook of Chinese Medicine Chemistry for Chinese Colleges of Traditional Chinese Medicine in the New Century (for Chinese Medicine Specialty), Kuang Hai-Xue p. 23, Chinese Press of Traditional Chinese Medicine (Jun. 30, 2003) (English translation of abstract and concise explanation of relevance from Foreign Office Action).

Cheng et al., *Chinese J. of Pharmaceuticals*, 21(10):435-436 (1990).

Kupchan et al., *J. Am. Chem. Soc.*, 94(20):7194-7195 (1972).

Zhang et al., *ACTA Pharmaceutica Sinica*, 28(2):110-115 (1993).

* cited by examiner

METHODS FOR ISOLATION OF TRIPTOLIDE COMPOUNDS FROM *TRIPTERYGIUM WILFORDII*

CROSS REFERENCE TO RELATED APPLICATIONS

This application is a 35 USC §371 application of International Application No. PCT/US2005/00388 filed Feb. 7, 2005, designating the United States, which claims priority to U.S. Application No. 60/543,236 filed Feb. 9, 2004, both of which are hereby incorporated by reference in their entirety.

FIELD OF THE INVENTION

The invention pertains to methods for extraction, isolation, and purification of triptolide and related molecules, such as tripdiolide and 16-hydroxytriptolide, from *Tripterygium wilfordii*.

REFERENCES

Z. Cheng et al., "Research on extraction technology of *Tripterygium*", Chinese J. of Pharmaceuticals 21(10):435-436 (1990).
S. M. Kupchan et al., "Triptolide and tripdiolide, novel antileukemic diterpenoid triepoxides from *Tripterygium wilfordii*", J. Am. Chem. Soc. 94(20):7194-7195 (1972).
S. M. Kupchan et al., U.S. Pat. No. 4,005,108 (1977).
P. E. Lipsky et al., U.S. Pat. No. 5,580,562 (December 1996).
K. Ren et al., U.S. Appn. Pubn. No. 20040018260 (January 2004).
T. T. Wiedmann et al., U.S. Pat. No. 5,843,452 (December 1998).
C. P. Zhang et al., "Studies on diterpenoids from leaves of *Tripterygium wilfordii*", Acta Pharmaceutica Sinica 28(2): 110-115 (1993).

BACKGROUND

Compounds derived from the Chinese medicinal plant *Tripterygium wilfordii* (TW) have been identified as having useful therapeutic properties, particularly immunosuppressive activity and anticancer activity. These compounds include triptolide, tripdiolide and 16-hydroxy triptolide. Synthetic derivatives and prodrugs of these compounds have also shown therapeutic activity, often in combination with improved pharmacological properties. See, for example, U.S. Pat. No. 5,468,772 (Tripterinin compound and method), U.S. Pat. No. 5,648,376 (Immunosuppressant diterpene compound), U.S. Pat. No. 5,663,335 (Immunosuppressive compounds and methods), U.S. Pat. No. 5,759,550 (Method for suppressing xenograft rejection), U.S. Pat. No. 5,843,452 (Immunotherapy composition and method), U.S. Pat. No. 5,962,516 (Immunosuppressive compounds and methods), U.S. Pat. No. 6,150,539 (Triptolide prodrugs having high aqueous solubility), U.S. Pat. No. 6,294,546 (Uses of diterpenoid triepoxides as an antiproliferative agent), U.S. Pat. No. 6,537,984 (Uses of diterpenoid triepoxides as an antiproliferative agent), U.S. Pat. No. 6,548,537 (Triptolide prodrugs having high aqueous solubility), U.S. Pat. No. 6,569,893 (Amino acid derivatives of triptolide compounds as immune modulators and anticancer agents), U.S. Pat. No. 6,599,499 (Uses of diterpenoid triepoxides as an antiproliferative agent), and U.S. Pat. No. 6,620,843 (Anticancer treatment using triptolide prodrugs), each of which is incorporated herein by reference.

Isolation of the native compounds from the plant material has, to date, typically required laborious extraction and purification procedures. Kupchan et al. (1972, 1977) describe a method in which the root material is extracted with ethanol, the solid extract is dissolved in ethyl acetate and partitioned with water, and the ethyl acetate fraction is chromatographed on silica gel. Cheng et al. (1993) describe a method in which the first extraction employs hot water, followed by addition of ethanol, filtration, removal of the ethanol, partitioning with chloroform, and chromatography on silica gel. The method described by Lipsky et al. (1996) employs subsequent extractions with chloroform, methanol, and toluene, with removal of solvent between each extraction, followed by chromatography on alumina and then on silica gel. Wiedmann et al. (1998) describe a method in which the root material is extracted with refluxing aqueous ethanol, the solid extract is partitioned between dichloromethane and water, and the dichloromethane phase is concentrated and chromatographed on silica gel. Ken et al. (2004) describe a method in which the root is extracted repeatedly with ethanol, and the extracts are concentrated and extracted repeatedly with chloroform, followed by chromatographic purification.

In isolation methods to date, the extraction steps generally produce an extract which retains large quantities of undesired materials, which then must be removed chromatographically, requiring large investments of time and materials. In view of the therapeutic utility of these compounds, higher efficiency methods for isolation and purification are desired.

SUMMARY OF THE INVENTION

The invention provides an improved method of isolating triptolide and related compounds, e.g. tripdiolide and 16-hydroxytriptolide, from *Tripterygium wilfordii* (TW) plant material. In accordance with the method, an extract of *Tripterygium wilfordii* plant material containing these compounds is formed and then purified. The extract is initially formed by (a) extracting TW plant material, preferably root material, with aqueous ethanol, and concentrating to obtain a residue; and (b) forming a slurry of this residue in an organic solvent, preferably a chlorinated hydrocarbon solvent, such as chloroform, methylene chloride, dichloroethane, or mixtures thereof; partitioning the slurry with water for a period of about 10 mins-10 hours; and then removing the water.

Typically, the extracting of step (a) includes three extractions with refluxing ethanol, each preferably using 4-5 mL of ethanol per g of plant material, followed by pooling of the extracts; the slurry formed in step (b) comprises 8-12 volumes of organic solvent relative to the residue; and the partitioning of step (b) employs ½ to 2 volumes of water relative to the slurry.

The subsequent purification comprises the steps of:
further partitioning the slurry with an aqueous solution of base, removing the aqueous solution of base, and removing at least a portion of the organic solvent from the slurry;
washing the residue with a lipophilic solvent; and
eluting the residue from a silica gel adsorbent.

In one embodiment, this purification comprises, following steps (a) and (b) above:
(c) partitioning the slurry with an aqueous solution of base, then removing the aqueous solution, and then removing the organic solvent, to obtain a further residue;
(d) washing the further residue with a hydrocarbon solvent, to obtain a solid product; and
(e) purifying the solid product by silica gel chromatography.

In another embodiment, this purification comprises, following steps (a) and (b) above:

(c) partitioning the slurry of the residue with an aqueous solution of base, removing the aqueous solution, and removing a portion of the organic solvent, to obtain a concentrated slurry;

(d) adding silica gel to the concentrated slurry, in an amount effective to adsorb the triptolide and related compounds;

(e) washing the residue and silica gel with a hydrocarbon solvent; and (f) eluting the triptolide and related compounds from the silica gel.

In a further embodiment, this purification comprises, following steps (a) and (b) above:

(c) removing the organic solvent from the slurry of the residue;

(d) washing the residue with a hydrocarbon solvent;

(e) forming a further slurry of the washed residue in an organic solvent selected from chloroform, methylene chloride, dichloroethane and mixtures thereof;

(f) partitioning the further slurry with an aqueous solution of base, then removing the aqueous solution, and then removing the organic solvent, to obtain a solid product; and (g) purifying the solid product by silica gel chromatography.

In the aqueous solution of base, the base is preferably a water soluble hydroxide, carbonate or bicarbonate having a counterion selected from lithium, sodium, potassium, cesium, ammonium, and tetraalkylammonium, where alkyl is preferably $C_1$-$C_4$ alkyl. Suitable bases include, for example, NaOH, KOH, $NaHCO_3$, $KHCO_3$, $Na_2CO_3$ and $K_2CO_3$. The solution may be selected, accordingly, from 0.1N-2.5N aqueous NaOH, 0.1N-2.5N aqueous KOH, 10%-15% aqueous $NaHCO_3$, and 12%-18% aqueous $KHCO_3$. The base partitioning is generally carried out for about 2 days, following a brief (e.g. 5-20 minutes, typically about 10 minutes) period of stirring. Optionally, following the removal of the aqueous solution of base, and prior to the removal of all or a portion of the organic solvent, the organic solvent is washed with a dilute aqueous acidic solution.

The lipophilic solvent is preferably a hydrocarbon solvent selected from linear, branched and cyclic hydrocarbons having 5-7 carbon atoms, and mixtures thereof; examples include hexane and cyclohexane. In one embodiment, the hydrocarbon solvent is hexane. The silica gel chromatography preferably employs a mobile phase comprising a nonpolar solvent, such as hexane, in combination with a more polar solvent, such as ethyl acetate.

DETAILED DESCRIPTION OF THE INVENTION

I. Overview

The invention provides a procedure for purifying an extract of *Tripterygium wilfordii* (TW) plant material containing triptolide and related compounds, such as tripdiolide and/or 16-hydroxytriptolide, and isolating these compounds. Other useful related compounds such as triptriolide, tripchlorolide, and triptonide may also be isolated.

As described further below, the method includes treatment of an initial organic extract with aqueous base, which removes a significant amount of impurities at an early stage of the process, thereby increasing yield and reducing production costs. The base treatment effectively removes acidic or weakly acidic compounds (e.g. celastrol, triptoquinone A, triptoquinone G, 3-hydroxyoleanolic acid, polpunonic acid, tripterygic acid A, and phenolic compounds such as triptonoterpene, hypolide, triptophenolide, and triptonodial) from the organic TW extract. The base treatment also remove "oily" impurities from the extract via saponification and/or hydrolysis. This step has been found to remove about 70% of the undesired impurities from the extract, including oily materials whose removal typically generates a large majority of the cost of subsequent purification using prior art methods.

The method of the invention also includes an extraction with a lipophilic solvent, such as cyclohexane or a similar hydrocarbon-based solvent, e.g. hexanes, pentanes, petroleum ether, etc., to remove less polar impurities from the extract. This step further simplifies the subsequent chromatographic purification steps, by removing components which would otherwise typically be removed chromatographically.

II. Extraction Procedure

The *Tripterygium wilfordii* (TW) extract is initially formed by (i) extracting ground, chopped or otherwise finely divided TW plant material with aqueous ethanol, and concentrating the liquid extract to obtain a residue; (ii) forming a slurry of this residue in an organic solvent, preferably a chlorinated hydrocarbon solvent, typically selected from chloroform, methylene chloride, dichloroethane and mixtures thereof; (iii) partitioning the slurry with water for a period of about 10 mins-10 hours; and (iv) removing the water from the slurry.

The plant material may include the roots, stems, and leaves of *Tripterygium wilfordii*; preferably, the root material is used. The TW plant is found in the Fujiang Province and other southern provinces of China; TW plant material can generally be obtained in China or through commercial sources in the United States.

Preferably, the ethanol extraction (i) includes three extractions with refluxing ethanol, each using 4-5 mL of ethanol per gram of plant material, followed by pooling of the extracts. The amount of organic solvent used, typically chloroform or dichloroethane, used in step (ii) is generally about 8-12 times the volume of the residue from step (i). The partitioning step (iii) generally employs ½ to 2 volumes of water relative to the volume of slurry.

As used herein, "partitioning" of a mixture of two immiscible fluids generally refers to a short period of stirring, e.g. about 10-30 minutes, more typically 10-15 minutes, followed by settling of the mixture, typically for a period of hours or days. In this case, the organic slurry and water are first stirred together, i.e. for about 10 minutes, and allowed to settle over a period of about 10 mins-10 hours, preferably about 2 hours.

III. Purification Procedure

In accordance with the method of the invention, the slurry obtained following step (iv) above is partitioned with an aqueous solution of base. In this process, the slurry and solution are first stirred together, i.e. for about 10 minutes, and allowed to settle over a period of about 10 mins-10 days, preferably about 1-4 days, more preferably about 2 days. The base is preferably a water soluble hydroxide, carbonate, or bicarbonate having a counterion selected from lithium, sodium, potassium, cesium, and ammonium. Suitable bases include, for example, NaOH, KOH, $NaHCO_3$, $KHCO_3$, $Na_2CO_3$ and $K_2CO_3$. In preferred embodiments, the aqueous solution of base is selected from 0.1-2.5N aqueous NaOH, 0.1-2.5N aqueous KOH, 10%-15% aqueous $NaHCO_3$, and 12%-18% aqueous $KHCO_3$.

The aqueous solution of base is removed, and then, optionally, the organic solvent is washed with a dilute aqueous acidic solution, e.g. 1% HCl. At least a portion of the organic solvent is then removed from the slurry.

The residue obtained, which may be substantially solid or a concentrated slurry, is then washed with a lipophilic solvent, followed by elution from a silica gel adsorbent. Preferably, the lipophilic solvent is a hydrocarbon solvent, preferably a saturated hydrocarbon, selected from linear, branched and cyclic hydrocarbons having 5-7 carbon atoms, and mixtures thereof. In one embodiment, the solvent is cyclohexane.

Note that in variations of the procedure, as described below, the order of certain treatment steps in the purification process may be altered.

Elution from a silica gel adsorbent (i.e. silica gel chromatography) preferably employs a solvent mixture, or mobile phase, comprising a non-polar solvent, such as a hydrocarbon, alkyl ether, or mixture thereof, in combination with a more polar solvent, such as an ester or ketone solvent. Such non-polar solvents include, for example, hexane, cyclohexane, petroleum ether, or THF. Such polar solvents include, for example, ethyl acetate, acetone, or methyl ethyl ketone (MEK). In one embodiment, the solvent mixture comprises cyclohexane and ethyl acetate. Solvent gradients may be used, in accordance with known methods.

IV. Variations on the Purification Procedure

In one embodiment, substantially all of the organic solvent is removed from the slurry following removal of the aqueous base, to give a solid or substantially solid residue. This residue is then washed with the lipophilic solvent to obtain a solid product, which is then purified by silica gel chromatography, as described above.

In another embodiment, only a portion of the organic solvent is removed from the slurry following removal of the aqueous base, to give a concentrated slurry. Silica gel is then added to the concentrated slurry, in an amount effective to adsorb triptolide and related compounds (e.g. tripdiolide and/or 16-hydroxytriptolide). The resulting mixture is then washed with the lipophilic solvent, and the triptolide and related compounds are then eluted from the silica gel.

In a further embodiment, extraction with the lipophilic solvent precedes the base treatment. Accordingly, prior to partitioning with base, the organic solvent is removed from the slurry obtained following step (iv) above, and the residue is washed with the lipophilic solvent. A further slurry of the washed residue is then formed, again in an organic solvent selected from chloroform, methylene chloride, dichloroethane and mixtures thereof, and this slurry is then partitioned with an aqueous solution of base, as described above, for a period of about 10 minutes to 10 days, preferably about 2 days. The aqueous base solution is removed, and substantially all of the organic solvent is then removed, to obtain a substantially solid residue, which is then purified by silica gel chromatography.

V. Exemplary Procedure

Following is an exemplary isolation procedure in accordance with one embodiment of the invention. This procedure is intended to illustrate and not to limit the invention.

A. Extraction
1. Dried TW biomass is ground into pieces (1×0.1 cm-5×0.5 cm (length×diameter) for root core and stem; 0.1-2.0 cm in size (chip shape) for root bark. The ground TW biomass is refluxed with 50-95% (preferably 90%) ethanol for 2-5 (preferably 3) hours, 2-5 (preferably 3) times, at a weight/volume ratio of solid/ethanol of 1:4-6 (preferably 1:5) for the first extraction and 1:3-5 (preferably 1:4) for the subsequent extractions.
2. The extracts are pooled, and the is ethanol removed under reduced pressure to give a dark slurry.

B. Isolation (Including Base Treatment and Hydrocarbon Extraction)
1. The slurry is suspended in 8-12, preferably 10, volumes of dichloroethane or chloroform.
2. Water is added, in an amount of ½-2 volumes, preferably ½ volume, to the suspension. The mixture is stirred for about 10 minutes and allowed to settle over a period of 1-10 hours, preferably 2 hours.
3. The water layer is removed, and ½-1 volume, preferably ½ volume, of 0.1-2.5N, preferably 0.5 N NaOH or KOH solution, or 10-15% $NaHCO_3$, is added to the organic phase. The mixture is stirred gently for about 10 minutes, then left for 1-10 days, preferably 4 days, to allow the layers to separate.
4. The aqueous phase is removed.
5. Water is added, in an amount of ¼-1 volume, preferably ¼ volume, relative to the organic phase. The mixture is stirred for about 10 minutes and left for 1-3 hours. Optionally, the mixture is washed twice at this stage with 1% HCl.
6. The aqueous phase is removed, and a drying agent, such as $Na_2SO_4$ or $MgSO_4$ (3 g/100 mL), is added to the organic phase. The mixture is stirred and then filtered to remove the drying agent.
7. The organic solvent is removed completely under reduced pressure.
8. Cyclohexane is added to the resulting solid, and the mixture is stirred, e.g. for about 10 minutes, to suspend the solid.
9. The solid is removed by filtration and dried under reduced pressure at 40-60° C. to obtain an intermediate product as a yellow powder.

C. Further Purification (Silica Gel Chromatography)
1. The powder is dissolved in 1:1 cyclohexane:ethyl acetate at a concentration of 0.5-1.0 g/mL, preferably 0.75 g/mL.
2. The dissolved material is loaded onto a pre-equilibrated silica gel column (200-300 mesh, 100×1-20 cm), using about 10 g of silica gel per 1-3 g, preferably per 2 g, of the powder intermediate.
3. The product is eluted using the same solvent mixture at a flow rate of 10-30 ml/hr, preferably 18 ml/hour. Triptolide-enriched fractions are collected, monitoring with TLC or HPLC.
4. Triptolide-enriched fractions are pooled and the solvent removed.

Typically, triptolide and/or related compounds are crystallized from the obtained product by temperature adjustment and/or solvent (e.g. acetone or ethyl ether) adjustment. Optionally, column chromatography and/or crystallization are repeated.

It is claimed:
1. A method for purifying an extract of *Tripterygium wilfordii* plant material containing triptolide and related compounds, wherein the extract is formed by
   (a) extracting plant material with aqueous ethanol, and concentrating to obtain a residue; and
   (b) forming a slurry of this residue in an chlorinated organic solvent; partitioning the slurry with water for a period of about 10 mins-10 hours; and then removing the water;
and said purifying comprises the steps of:
   (c) further partitioning the slurry with an aqueous solution of base, removing the aqueous solution of base, and removing at least a portion of the organic solvent from the slurry;

(d) washing the product of step (c) with a lipophilic solvent; and (e) eluting the washed product from step (d) from a silica gel adsorbent.

2. The method of claim 1, wherein step (c) comprises, following the removal of the aqueous solution of base, removing the organic solvent to obtain a further residue;

(d) washing the further residue with a hydrocarbon solvent to obtain a solid product; and (e) purifying the solid product by silica gel chromatography.

3. The method of claim 2, wherein a mobile phase comprising cyclohexane and ethyl acetate is used for said silica gel chromatography.

4. The method of claim 1, wherein said purifying comprises the steps of:

(c) partitioning the slurry of the residue with an aqueous solution of base, removing the aqueous solution, and removing a portion of the organic solvent, to obtain a concentrated slurry;

(d) adding silica gel to the concentrated slurry, in an amount effective to adsorb the triptolide and related compounds;

(e) washing the residue and silica gel with a hydrocarbon solvent; and (f) eluting the triptolide and related compounds from the silica gel.

5. The method of claim 1, wherein said purifying comprises the steps of:

(c) removing the organic solvent from the slurry of the residue;

(d) washing the residue with a hydrocarbon solvent;

(e) forming a further slurry of the washed residue in an organic solvent selected from chloroform, methylene chloride, dichloroethane and mixtures thereof;

(f) partitioning the further slurry with an aqueous solution of base, then removing the aqueous solution, and then removing the organic solvent, to obtain a solid product; and (g) purifying the solid product by silica gel chromatography.

6. The method of claim 1, wherein the extracting of step (a) includes three extractions with refluxing ethanol, each using 4-5 mL of ethanol per g of plant material, followed by pooling of the extracts.

7. The method of claim 1, wherein the chlorinated organic solvent is selected from the group consisting of chloroform, methylene chloride, dichloroethane and mixtures thereof.

8. The method of claim 1, wherein the slurry formed in step (b) comprises 8-12 volumes of organic solvent relative to the residue, and the partitioning of step (b) employs ½ to 2 volumes of water relative to the slurry.

9. The method of claim 1, wherein the base is a water soluble hydroxide, carbonate or bicarbonate having a counterion selected from lithium, sodium, potassium, cesium, ammonium, and tetraalkylammonium.

10. The method of claim 9, wherein the base is selected from NaOH, KOH, $NaHCO_3$, $KHCO_3$, $Na_2CO_3$ and $K_2CO_3$.

11. The method of claim 10, wherein the aqueous solution of base is selected from 0.1N-2.5N aqueous NaOH, 0.1N-2.5N aqueous KOH, 10%-15% aqueous $NaHCO_3$, and 12%-18% aqueous $KHCO_3$.

12. The method of claim 1, wherein the partitioning with the aqueous solution of base is carried out for about 2 days.

13. The method of claim 1, wherein, following the removing of the aqueous solution of base and prior to the removing of at least a portion of the organic solvent, the organic solvent is washed with a dilute aqueous acidic solution.

14. The method of claim 1, wherein the hydrocarbon solvent is selected from linear, branched and cyclic hydrocarbons having 5-7 carbon atoms, and mixtures thereof.

15. The method of claim 14, wherein the hydrocarbon solvent is cyclohexane.

16. The method of claim 1, wherein the plant material comprises root material.

17. The method of claim 1, wherein the related compounds comprise tripdiolide and/or 16-hydroxytriptolide.

* * * * *